United States Patent [19]

Schlesinger et al.

[11] Patent Number: 5,091,309
[45] Date of Patent: Feb. 25, 1992

US005091309A

[54] SINDBIS VIRUS VECTORS

[75] Inventors: Sondra Schlesinger; Henry V. Huang, both of St. Louis, Mo.; Robin Levis, Takoma Park, Md.; Barbara Weiss, Clayton; Manuel Tsiang, St. Louis, both of Mo.

[73] Assignee: Washington University, St. Louis, Mo.

[21] Appl. No.: 395,007

[22] Filed: Aug. 17, 1989

Related U.S. Application Data

[63] Continuation-in-part of Ser. No. 819,647, Jan. 16, 1986, abandoned.

[51] Int. Cl.[5] .................. C12P 21/00; C12P 19/34; C12N 15/00; C12N 7/00
[52] U.S. Cl. ...................... 435/69.1; 435/91; 435/172.3; 435/235.1; 435/240.2; 435/320.1; 435/948; 536/27; 935/32; 935/57; 935/60; 935/70
[58] Field of Search ............ 435/91, 172.3, 69.1, 435/235, 240.2, 320.1, 948; 536/27; 935/32, 57, 60, 70

[56] References Cited
U.S. PATENT DOCUMENTS
4,719,177  1/1988  Baltimore et al. .................. 435/91

OTHER PUBLICATIONS

Mackett et al. (1984), Journal of Virology, vol. 49, pp. 857–864.
Monroe et al. (1982), Journal of Virology, vol. 41, pp. 153–162.
R. Levis et al., Cell 44:137 (1986).
C. Xiong et al., Science 243:1188 (1989).
R. Levis et al., Proc. Natl. Scad. Sci. U.S.A. 84:4811 (1987).

Primary Examiner—Jacqueline Stone
Assistant Examiner—Gian Wang

[57] ABSTRACT

The present invention relates to RNA vectors comprising Sindbis virus DI RNA having inserted therein heterologous RNA. The vectors of the present invention provide for the cloning and expression of heterologous RNA in eucaryotic cells as well as the packaging of heterologous RNA into viral particles in the presence of helper virus. Transformed cells and genetically altered alphavirus particles comprising alphavirus DI RNA having inserted therein heterologous RNA are also provided.

14 Claims, 7 Drawing Sheets

FIGURE 1

```
         10         20         30         40         50         60         70         80         90        100
GGATATAGTGGTGAGTATCC CCGCCTGTCACGCGGAGAC CGGGGTTCGGTTCCCCGACG GGGAGCCAAACAGCCGACCA ATTGCACTACCATCACAATG 110        120        130        140        150        160        170        180        190        200
GAGAAGCCAGTAGTAAACGT AGACGTAGACCCCCAGAGTC CGTTTGTCGTGCAACTGCAA AAAGCTTCCCGCAATTTGAG GTAGTAGCACAGCAGGTCAC 210        220        230        240        250        260        270        280        290        300
TCCAAATGACCATGCTAATG CCAGAGCATTTTCGCATCTG GCCAGTAAACTAATCGAGCT GGAGGTTCCTACCACAGCGA CGATCTTGGACATAGGCAGC 310        320        330        340        350        360        370        380        390        400
GCACCGGCTCGTAGCATGTT TTCCGAGCACCAGTATCATT GTGTCTGCCCCATGCGTAGT CCAGAAGACCCGGACCGCAT GATGAAATATGCCAGTAAAC 410        420        430        440        450        460        470        480        490        500
TGGCGGAAAAAGCGTGCAAG ATTACAAACAAGAACTTGCA TGAGAAGATTAAGGATCTCC GGACCGTACTTGATACGCCG GATGCTGAAACACCATCGCT 510        520        530        540        550        560        570        580        590        600
CTGCTTTCACAACGATGTTA CCTGCAAATATGCCAGTAAA CTGGCGGAAAAAGCGTGCAA GATTACAAACAAGAACTTGC ATGAGAAGATTAAGGATCTC 610        620        630        640        650        660        670        680        690        700
CGGACCGTACTTGATACGCC GGATGCTGAAACATCGC TCTGCTTCACAACGATGTT ACCTGCAACATGCGTGCCGA ATATTCCGTCATGCAGGACG 710        720        730        740        750        760        770        780        790        800
TGTATATCAACGCTCCCGGA ACTACAACACCAACTGGGCC GACGAGAAAGTCCTTGAAGC GCGTAACATCGGACTTTGCA GCACAAAGCTGAGTGAAGGT 810        820        830        840        850        860        870        880        890        900
CGGACCGTACTTGATACGCC GGATGCTGAAACATCGC TCTGCTTCACAACGATGTT ACCTGCAACATGCGTGCCGA ATATTCCGTCATGCAGGACG

910        920        930        940        950        960        970        980        990       1000
GCTTGCAGAGCTGGCATCTT CCATCGGGTGTTCCACTTGA ATGAAAGCAGTCGTACACTT GCCGCTGTGATACAGTGGTG AGTTGCGAAGGCTACGTAGT

1010       1020       1030       1040       1050       1060       1070       1080       1090       1100
GAAGAAATCACCATCAGTC CCGGGATTCACGGGAGAAAC CGTGGGATACGCGGTTACAC ACAATAGCGAGGGCTTCTTG CTATGCAAAGTTACTGACAC 1110       1120       1130       1140       1150       1160       1170       1180       1190       1200
AGTAAAGGAGAACGGGTAT CGTTCCCTGTGTGCACGTAC ATCCCGGCCACCATGCGA TCAGATGCGATCGGTATAATGG CCACGGATATATCACCTGAC
```

SINDBIS VIRUS VECTORS

CROSS-REFERENCE TO RELATED APPLICATIONS

This application is a continuation-in-part of application Ser. No. 06/819,647, filed Jan. 16, 1986 now abandoned.

TECHNICAL FIELD

The present invention relates to the incorporation of nucleic acid molecules into cellular systems, the vectors effecting such incorporation and to those cells comprising such vectors. This invention further relates to the incorporation of nucleic acid molecules into viral particles, the vectors effecting such incorporation and to the viral particles comprising such vectors.

BACKGROUND OF THE INVENTION

Advances in recombinant DNA technology and genetic engineering have provided means for producing in bacteria specific proteins of commercial and economic importance. In many instances, bacteria are unable to consistently provide the post-translational modifications such as proper protein folding, glycosylation, protein processing (e.g. enzymatic cleavage) and the like required for functional eucaryotic protein production. Indeed, studies in eucaryotic cells of such post-translational modifications as glycosylation indicate that the specific post-translational modification may even vary depending upon the eucaryotic cell type doing the modifying. This host cell dependent variability is significant as differences in, for example, protein glycosylation, may result in production of antigenically and/or functionally different proteins. It is, therefore, desirable to develop eucaryotic cell systems (e.g. eucaryotic host-vector systems) which can provide the desired and/or required post-translational modifications and thus become efficient factories for functional and/or antigenically homologous protein production.

A key element in the genetic engineering of both procaryotic and eucaryotic cells to effect the production of a desired protein is the development of defined vectors and host-vector systems. "Vector(s)" or "vector system(s)" are herein defined as nucleic acid molecules capable of introducing a heterologous nucleic acid into a host cell. "Heterologous" when applied to a nucleic acid (e.g. DNA and/or RNA) is herein understood to mean a nucleic acid sequence wherein all or a portion of the sequence or its complement are not normally present in the vector employed to introduce the heterologous nucleic acid into a host cell. A "cloning vector" is herein understood to mean a vector which permits the replication of heterologous nucleic acid within a host cell. An "expression vector" is herein understood to mean a vector which permits the production, in a host cell, of a protein or fragment thereof encoded in the heterologous nucleic acid sequence. The term "host-vector system" is herein understood to mean a host cell capable of accepting and allowing the replication and expression of genetic information carried by a vector.

A number of eucaryotic vector systems have been developed, all are viral vectors, all replicate through a DNA intermediate, and all have some limitation which renders them each less than ideal for expression and/or cloning of heterologous nucleic acid(s). These limitations include high frequencies of spontaneous mutations, Ashman and Davidson (1984); Calos et al. (1983), low levels of expression, Rigby (1983), limited host range and decreased efficiency of heterologous nucleic acid expression due to nuclear regulatory mechanisms such as chromatin structure, transcriptional regulation, polyadenylation, RNA processing and RNA transport to the cytoplasm. Although the poxvirus vector system bypasses all the limitations of nuclear regulation, this system is tedious to work with using currently available methodologies. Thus, while a number of vectors have been developed to replicate and express heterologous nucleic acid in eucaryotic host cells, there is a continued need for eucaryotic vectors able to permit rapid and efficient heterologous nucleic acid expression in a wide range of host cells. Employment of a ssRNA virus genome as a vector would certainly facilitate efficient and rapid expression of heterologous nucleic acid (e.g. RNA) that otherwise may be expressed poorly due to nuclear regulatory mechanisms.

The present invention provides vectors comprising RNA molecules derived from alphavirus genomes and, specifically, from alphavirus defective interfering (DI) RNA. The alphavirus genus of the Togaviradae family includes more than 20 distinct viruses, Schlesinger (1980), the genomes of which comprise a single plus (+) strand RNA molecule which, unlike the current viral genomes employed as eucaryotic vectors, replicates soley through an RNA intermediate. Alphavirus gene expression and viral replication are independent of the host cell nucleus. Additionally, all alphaviruses studied to date have the ability to replicate in a wide range of vertebrates including both avian and mammalian hosts. Sindbis virus, one well-studied member of the alphavirus group, for example, infects all warm-blooded animal (avian and mammalian) cells tested and, in addition, has been shown to infect viper (reptilian) cells, Clark et al. (1973), as well as a large number of mosquito speceis, a fowl mite (*Bdellonyssus bursa*) and *Drosophila melanogaster*, Bras-Herring (1975) (1976). Thus, vectors derived from alphaviruses would offer a wide latitude in the choice of host cell consistent with synthesizing a particular product (e.g. protein) of interest. To date, there have been no reports nor teaching of how to construct a vector comprising an alphavirus genomic RNA molecule having inserted therein heterologous RNA.

Furthermore, like many other viruses, alphaviruses exhibit another interesting feature. Specifically, when passaged at high multiplicity in cultured cells, alphaviruses accumulate deletion mutants characterized by their ability to interfere with the replication of standard virus. These mutants are defined as defective interfering or DI particles. Perrault (1981). Depending upon the cells and the conditions of passaging, the first detectable DI particles appear after about three to five high multiplicity passages. The DI RNA contained within these DI particles is about one half the size of standard or virion RNA. Guild and Stollar (1977); Stark and Kennedy (1978). These molecules soon disappear on subsequent passaging and are replaced by molecules one-fourth to one-fifth the size of the original viral genome. In addition to the variable size of the DI RNA's generated by repeated high multiplicity infection of cultured cells by standard virus, the alphavirus DI genomes have been demonstrated to contain a heterogeneous and complex nucleic acid structure. Pettersson (1981). Notwithstanding the heterogeneous size and genome complexity of alphavirus DI RNA's, the biologic life cycle of the DI RNA's suggests that all DI virus genomes should contain the necessary sequences for DI RNA replication and packaging in the presence of helper virus (e.g. coinfection with standard virus). The sequences necessary for either DI or standard virus RNA replication and packaging, however, have not yet been elucidated.

Accordingly, it is an object of the present invention to provide alphavirus DI RNA sequences which permit alphavirus DI RNA replication and packaging in the presence of helper virus.

It is another object of the present invention to provide a vector comprising alphavirus DI RNA having inserted therein heterologous RNA.

It is still another object of the present invention to provide genetically altered alphavirus particles and/or cells comprising alphavirus DI RNA having inserted therein heterologous RNA.

It is yet a further object of the present invention to provide methods and compositions which permit the packaging of heterologous RNA into alphavirus virions.

These and other objects of the invention will be more fully apparent from the following general and detailed description of the invention.

SUMMARY OF THE INVENTION

The present invention relates to vectors comprising alphavirus DI RNA having inserted therein heterologous RNA. In one embodiment of the present invention, the alphavirus DI RNA comprises a Sindbis virus DI RNA genome or portion thereof.

In other embodiments of the present invention, cloning and expression vectors are provided comprising alphavirus DI RNA or a portion thereof having inserted therein heterologous RNA. In another embodiment of the present invention, the cloning and/or expression vectors of this invention permit the incorporation of heterologous RNA into alphavirus virions in the presence of helper virus or a helper cell line.

In yet another embodiment of the present invention, alphavirus DI RNA sequences are provided which permit alphavirus DI RNA replication and packaging in the presence of helper virus or a helper cell line.

In a further embodiment of the present invention, genetically altered alphaviruses and/or cells comprising alphavirus DI RNA having inserted therein heterologous RNA sequences are provided.

BRIEF DESCRIPTION OF THE DRAWINGS

In the following diagramatic representations, the DNA sequences are provided in a 5' to 3' orientation. Relevant restriction endonuclease sites are also shown. The DNA regions marked as described below are for purposes of diagramatic representation only and are not drawn to scale unless otherwise noted. The numbering of the DNA sequences from 5' to 3' is for diagramatic purposes only.

FIG. 1 depicts the DNA sequence of the DI-25 cDNA. The nucleotides underscored by a broken line denote restriction endonuclease cleavage sites. Nucleotide 2314 is the end of the DI cDNA. The C Region following the poly A region is leftover from cloning and unnecessary. Downstream from the poly A region, 2354-2360, is a Pst restriction site for linearizing the cDNA for transcription.

FIG. 2 depicts a map of plasmid KDI-25. The open segment represents bacterial sequences comprising an origin of replication (ori) and the ampicillinase gene ($Amp^R$). The solid black segment represents the promoter region for the SP6 polymerase (SP6 promoter). The directional arrow denotes the start and direction of RNA transcription of the DI-25 cDNA. The hatched segment denotes the cDNA sequences of a DI-25 RNA of Sindbis virus. The hatched segment is also shown in the linear diagram with relevant restriction enzyme sites indicated.

FIG. 3 depicts a deletion map of the genome of a Sindbis DI RNA. The deletions, which cover the entire DI genome are all indicated on this diagram. The open boxes represent regions which were deleted without causing a loss of biological activity. The closed boxes are regions which when deleted led to a loss in biological activity.

FIG. 4 depicts the construction of plasmid KDI-25 comprising a cDNA clone of a DI RNA of Sindbis virus. The details of each of these steps is described in Experimental Procedures. The hatched area denotes sequences from K11. The area that is darkened in the hatched fragments directly upstream from the HphI site indicates DNA sequences encoding the SP6 promoter. The darkened area denotes Sindbis virus DI cDNA.

DETAILED DESCRIPTION OF THE INVENTION

The RNA vectors of the present invention provide a means for replicating and expressing heterologous nucleic acid independent of the host cell nucleus in a broad phylogenetic range of host cells. This vector-mediated incorporation of heterologous nucleic acid into a host cell is herein from time-to-time, referred to as a "transfection" or "infection" of a host cell, where "transfection" means use of naked RNA and "infection" means use of virus particles. Accordingly, a host cell comprising heterologous nucleic acid is often referred to herein as a "transfected" or "infected" host cell.

The vectors of the present invention additionally permit the incorporation of heterologous nucleic acid into virus particles thereby providing a means for amplifying the number of infected host cells and, thus, heterologous protein production and heterologous nucleic acid replication therein. A "heterologous protein" is herein defined as a protein or fragment thereof wherein all or a portion of the protein is not encoded in the nucleic acid sequence of the vector employed to transfect or infect a host cell.

A "helper cell" is herein defined as a host cell capable of providing the replication and/or packaging functions otherwise provided by a helper virus. These methods and compositions may be described, briefly, as follows. DI particles of a specific alphavirus are generated by high multiplicity infection of cultured cells by techniques known to those skilled in the art. Perrault (1981). The DI RNA's are then isolated, Monroe and Schlesinger (1984), and a complete complementary DNA (cDNA) synthesized. Maniatis et al. (1982). The DI cDNA's are then converted into double-stranded (ds) cDNA, Maniatis et al. (1982), and the ds DNA's are then inserted into a bacterial cloning vector. Maniatis et al. (1982). Any cloning vector, bacterial, yeast or eucaryotic in origin, known and available to those skilled in the art may be employed including vectors that contain a DNA dependent RNA polymerase promoter. Cloning of the ds DI DNA in bacterial, yeast, or eucaryotic vectors known to those skilled in the art provides a means for generating a large number of ds DI cDNA molecules for the further manipulations described herein. The ds DI DNA molecules are then removed in their entirety by restriction endonuclease cleavage, Maniatis et al. (1982), from the cloning vector and inserted into a vector capable of directing DNA-dependent RNA transcription of the entire DI cDNA molecule. Such vectors currently available comprise the bacteriophage SP6 promoter, bacteriophage T3 promoter, bacteriophage T7 promoter, or an *E. coli* DNA dependent RNA polymerase promoter. In one preferred embodiment of the present invention, a vector containing the SP6 promoter was employed. Next, as described more fully in the examples below, various regions of the DI cDNA are deleted and then RNA transcripts generated by in vitro transcription of complete and deleted DI cDNA's. The RNA transcripts are then employed to transfect host cells permissive for replication and packaging of the specific alphavirus in the presence of a homologous or closely related helper (e.g. standard) alphavirus. As previously discussed, helper cells may alternatively be employed as host cells thereby obviating the need for the presence of a homologous or closely related helper (e.g. standard) alphavirus during the transfection with the RNA transcripts. After one or two passages, DI RNA containing the sequences essential for DI RNA replication and packaging will become the major viral RNA species in infected cells. Using this transfection and amplification assay, deletions covering the entire DI genome may be screened and the DI RNA sequences essential for DI replication and packaging determined.

Figure 1:
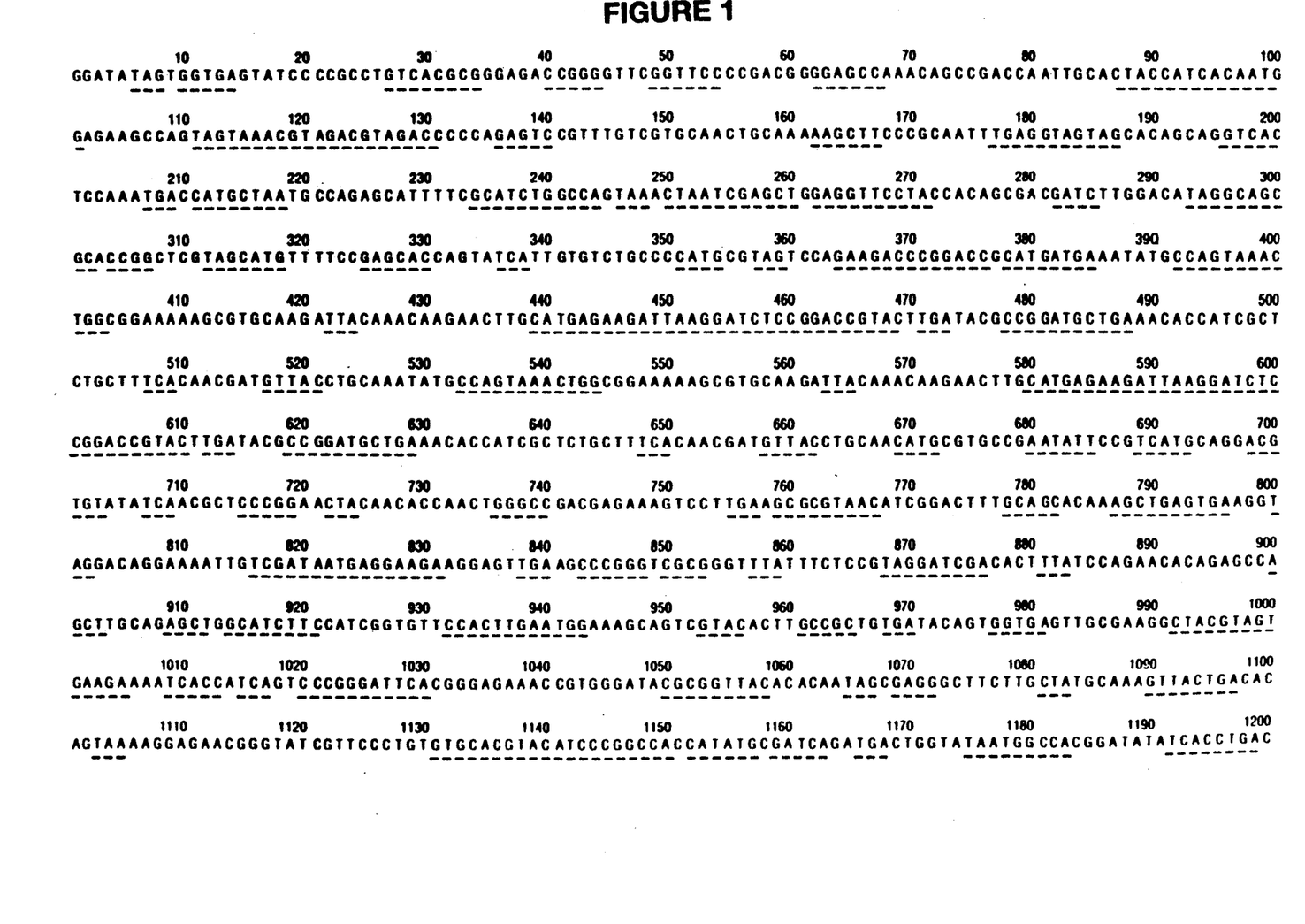
Figure 2:
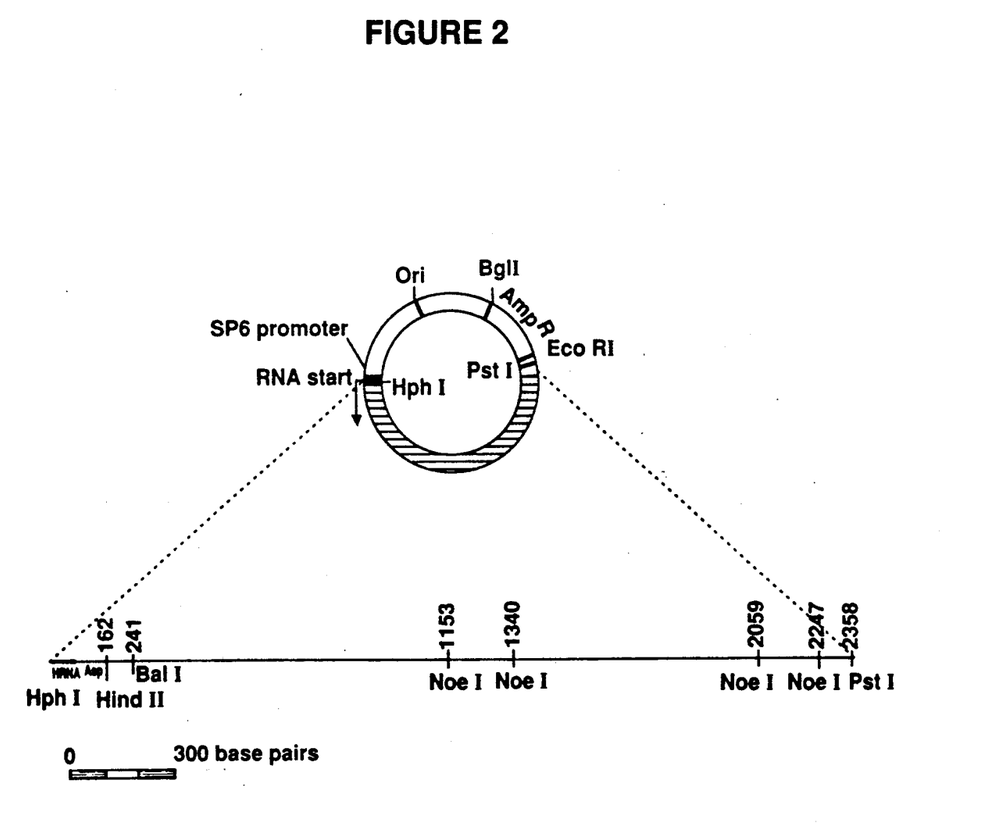
Figure 4:
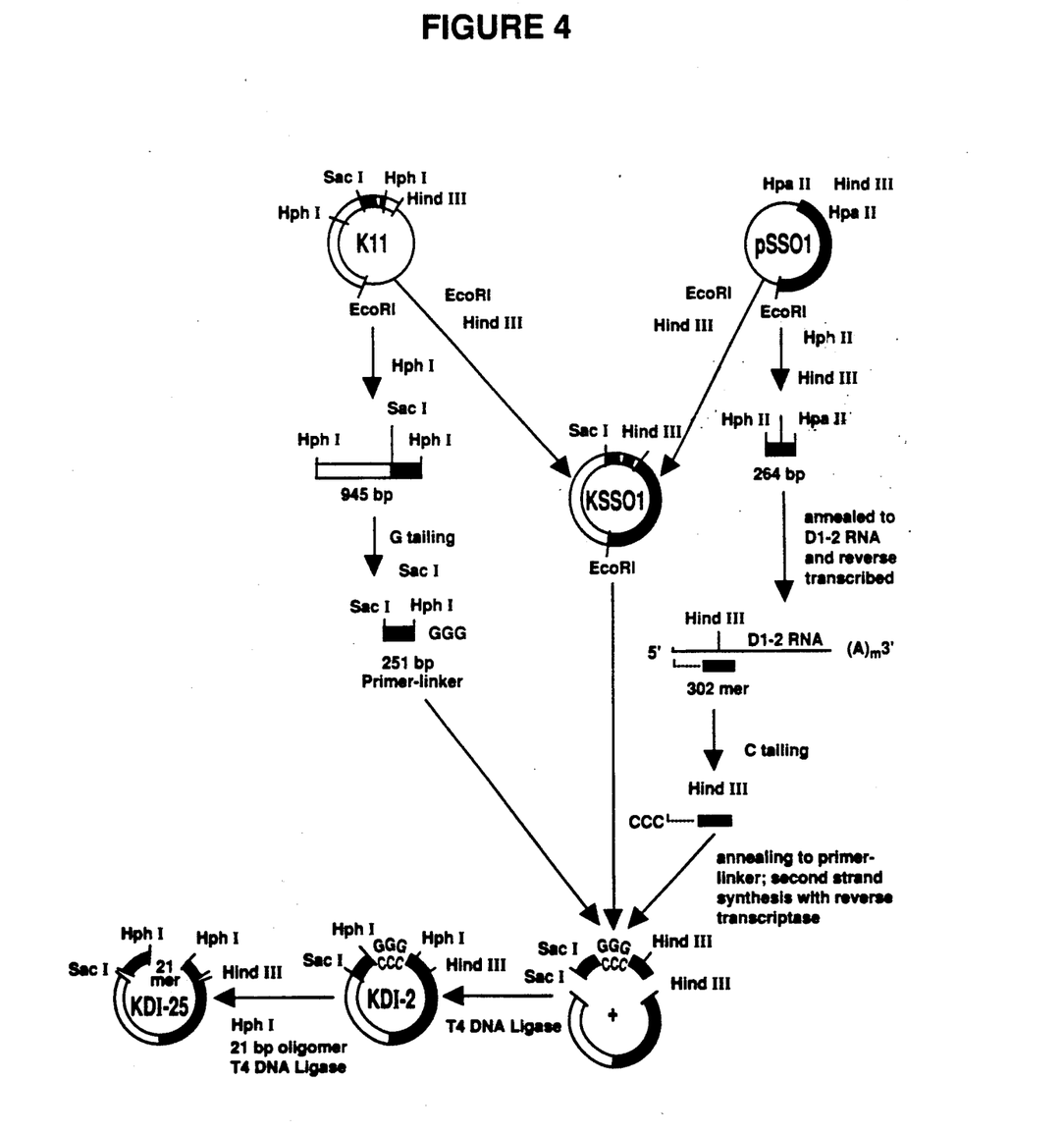

In one preferred embodiment, DI RNA molecules were isolated from Sindbis virus DI particles generated by high multiplicity infection in chick embryo fibroblasts (CEF). Monroe and Schlesinger (1984). The Sindbis virus DI RNA was then converted into cDNA, Maniatis et al. (1982); Monroe and Schlesinger (1984). The DI cDNA's were then converted into ds DNA molecules in accordance with procedures described in Maniatis et al. (1982). The ds DI cDNA molecules were then inserted into a bacterial cloning vector in order to generate multiple copies of DI cDNA. The plasmid with the cloned insert was designated pSS01. Monroe and Schlesinger (1984). As shown in FIG. 4 and described more fully in the examples below, the Sindbis virus DI cDNA was then removed from the cloning vector and inserted into a plasmid which contained a promoter for the SP6 bacteriophage DNA dependent RNA polymerase. The complete cDNA sequence of the Sindbis virus DI cDNA contained within this plasmid is given in FIG. 1. The resultant plasmid was designated KDI-25 (FIG. 4). The pertinent landmarks of the KDI-25 plasmid are: (i) the promoter for the SP6 bacteriophage polymerase positioned directly upstream from the 5' end of the Sindbis virus DI cDNA; (ii) the restriction enzyme sites downstream from the 3' terminus where the DNA was linearized to permit runoff transcription; and (iii) specific sites for restriction enzymes which were used to make deletions throughout the genome (FIG. 2).

The KDI-25 plasmids comprising the SP6 promoter and DI cDNA were then isolated; Maniatis et al. (1982), and the DI cDNA transcribed into RNA in vitro as described more fully in the examples below. The RNA transcripts from the KDI-25 plasmid were designated DI-25 RNA. The DI-25 RNA was then transfected into chick embroyo fibroblasts in the presence of helper Sindbis virus as described more fully in the examples below. After one to two passages, the DI RNA became the major viral RNA species in infected cells.

Figure 3:
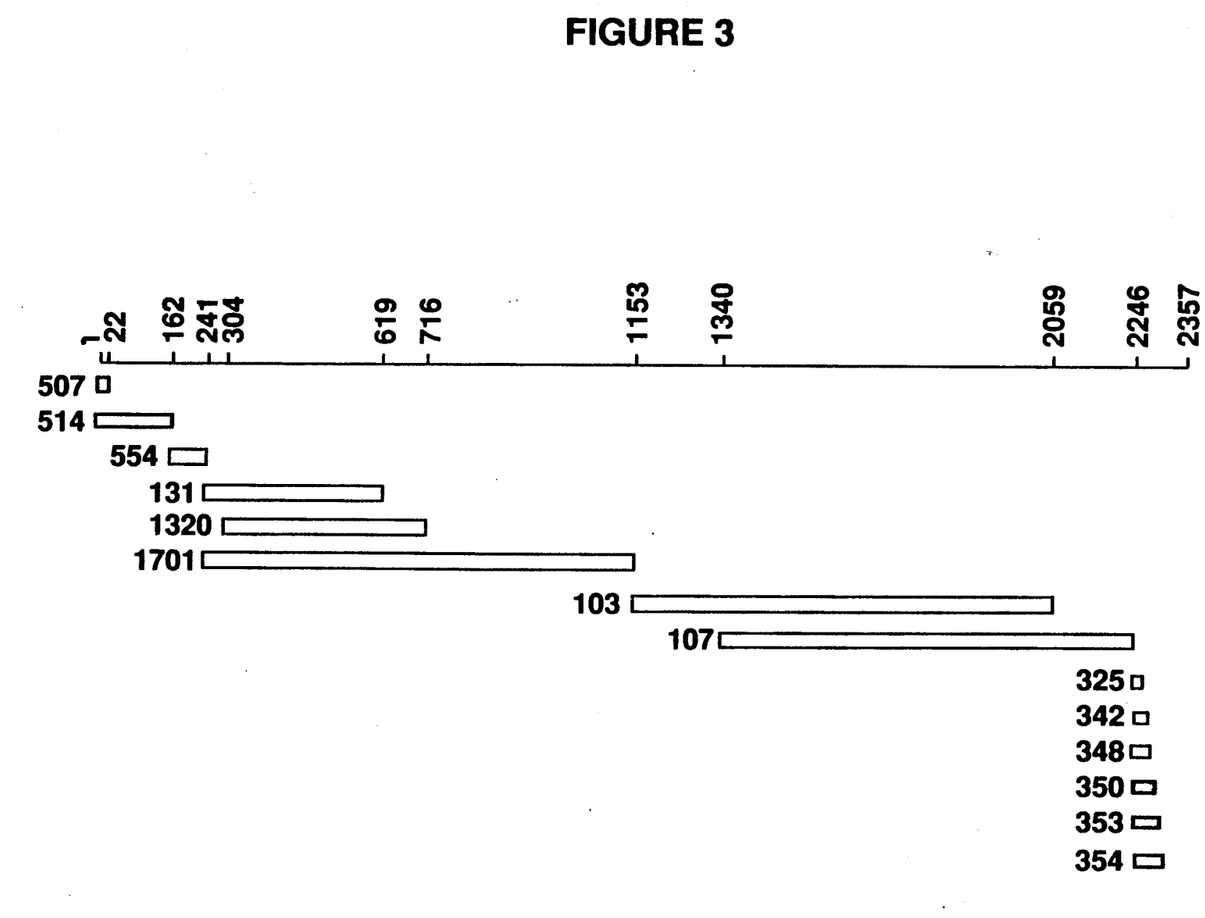

Using this transfection and amplification assay, a series of deletions covering the entire DI genome were screened to ascertain which RNA sequences in the DI-25 RNA molecules were essential for DI RNA replication and packaging. A summary of the deletions made and their effect on the viability (e.g. replication and packaging) of the RNA is presented in FIG. 3. The nucleotides from about 1928 to at least nucleotide 2314, followed by a poly A tail (FIG. 1) and from about nucleotide 1 to at least nucleotide 241 at the 5' terminus (FIG. 1) are the only nucelotide sequences required for replication and packaging of these DI genomes. The poly A tail will vary in length with at least 21 preferred. The poly A tail (an oligonucleotide formed from adenosine residues) is important for the stability of the RNA. The term "essentially pure" when used to define these DI RNA sequences means an essentially purified state. Specifically, the term means that these sequences are no longer contiguous with the DI RNA sequences with which they are naturally contiguous within a DI RNA genome.

Deletions in the internal regions of the transcribed RNA did not lead to a loss of biological activity. The large deletions did result in the DI RNA becoming heterogeneous after amplification and, in particular, becoming larger. Evolution of naturally-occurring DI RNAs from small to large has been observed and was thought to be due to an increase in the number of repeats present in the molecule. Kääriäinen et al. (1981). There is evidence of constraints on the size of DI RNAs that can be packaged, Guild and Stollar (1977) and naturally-occurring DI RNAs of the size described in Table 3, have not been found in DI particles. Stark and Kennedy (1978) reported that a small DI RNA detected intracellularly was not packaged. One possibility to explain the heterogeneity in the DI RNAs with large internal deletions is that they are packaged so poorly that larger DI RNAs arising during replication have a selective advantage in amplification. In addition, the small DI RNAs may be intrinsically unstable during replication. An important conclusion, however, is that more than 90% of the sequences in the DI RNA have no essential role in the replication or packaging of the molecule.

This conclusion is significant as it suggests that a large (e.g. at least 1500 nucleotide) fragment comprising, for example, heterogeneous RNA may be inserted into the DI RNA in place of those sequences not required for replication and packaging. Insertion of such heterogeneous RNA sequences should comply with the packaging constraints of DI RNA molecules and thereby afford a means for constructing a cloning vector and/or expression vector comprising alphavirus DI RNA having inserted therein heterogeneous RNA. As described more fully below, such cloning and expression vectors have been constructed by the methods and compositions of the present invention. Thus, the present invention now provides for the construction of RNA vectors comprising alphavirus DI RNA having inserted therein heterologous RNA. Furthermore, the present invention provides methods and compositions which enable the vectors of the present invention to permit replication and expression of heterologous RNA in eucaryotic cells and the packaging of heterologous RNA into virus particles.

The 5' terminus of the DI RNA has two regions of interest—the extreme 5' end and the 51 conserved nucleotides located from nucleotides 155 to 205 in the virion RNA. Ou et al. (1983). The observations that naturally-occurring DI RNAs varied at the 5' terminus, Tsiang et al. (1985), and that this latter region was the least conserved among alphaviruses, Ou et al. (1983) led to the proposal that the 51 nucleotide region played a crucial role in one or both functions of replicase binding and of encapsulation. A plausible model would be one in which the replicase first bound to this site on the negative strand and then initiated transcription at the exact 3' terminus. A precedent for a replicase binding specifically to internal sites on the RNA stems directly from the studies with the replicase of Qβ bacteriophage. Kamen (1975). Our finding that the highly conserved region in Sindbis RNA was not required for the replication of two different DI RNA molecules —one with the same 5' terminus as virion RNA and one with tRNA$^{Asp}$ sequences at the 5' terminus-makes the original proposal unlikely.

The premise that strong conservation of a nucleotide sequence is indicative of its having an essential function still may be valid. Thus, one explanation for our results is that this region has a function required for virus replication, but not for DI RNA replication. Two potential roles are in the synthesis of the 26S subgenomic RNA and in the translation of virion RNA. We cannot rule out the possibility, however, that the replication or packaging of DI RNA is distinct from that of virion RNA. It may be possible to resolve this point with a biologically-active cDNA clone of virion RNA. Since these sequences also carry out a coding function in virion RNA, deletions would inactivate the translational capacity of the molecule and only changes that did not affect the codon reading could be tested.

Although the 51 nucleotide conserved sequence was not essential for the biological activity of DI RNA, sequences further upstream from this region were required. A cDNA with a deletion of the first 7 nucleotides and one with a deletion from nucleotides 22 to 162, (FIGS. 1 and 3), produced RNA transcripts that were poorly viable. The 5' terminal 7 nucleotides are part of the tRNA$^{Asp}$ sequence which is not present either in several other DI RNAs or in Sindbis virion RNA and may be only one of several sequences able to be recognized at the 5' terminus. Based on their comparisons of the exact 5' terminus of several different alphaviruses, Ou et al. (1983) suggested that the structural features of the termini may be more important than the actual sequence and our data are consistent with this possibility. Thus, sequences providing a structure essentially equivalent to the structure provided by the sequences required for replication and packaging of DI RNA molecules in the presence of helper virus described herein are believed to constitute equivalents to the required sequences provided herein.

We have identified a maximum of 241 nucleotides at the 5' terminus and 430 nucleotides at the 3' terminus required for the biological activity of Sindbis DI RNAs. A DI RNA transcript containing essentially just these regions was not detected in the amplification assay, but this negative result may be due to packaging constraints on a molecule of this size. As stated previously, presumably other sequences could be substituted for the deleted ones producing a molecule of the right size that would be replicated and packaged. Indeed, as previously stated and described more fully below, other (e.g. heterologous) RNA sequences, when substituted for the deleted sequences, do permit replication and packaging of DI RNA in the presence of helper virus.

This finding is significant as it now provides for the construction of a cloning vector comprising nucleotides 1 to at least 241, and nucleotides from about 1928 to at least 2314, followed by a poly A tail (shown in FIG. 1) and heterologous RNA. Specifically, the present invention demonstrates that heterologous RNA comprising up to at least 1492 nucleotides in length inserted between nucleotides 241 and 1928 (FIGS. 1 and 2) were both replicated in transformed cells and packaged into Sindbis virus DI particles. The ability to package, in viral particles, heterologous RNA with this Sindbis virus DI vector provides for significantly amplified replication of heterologous RNA contained within the described vector. Indeed, in one preferred embodiment of the present invention, a heterologous DNA sequence encoding the E. coli enzyme chloramphenicol acetyl transferase (CAT) was inserted in place of DI sequences contained between the Bal I to SmaI restriction endonuclease sites in the DI cDNA, FIG. 2. The resultant plasmid comprising DI cDNA having inserted therein, heterologous DNA (CAT gene) was then transcribed into RNA comprising DI RNA having inserted therein heterologous RNA. The transcribed RNA representing a DI RNA vector was then employed to effect the replication and expression of the CAT gene in chick embryo fibroblasts and to effect the packaging of the CAT gene RNA transcript into DI particles.

Our finding that replication and packaging of CAT sequences inserted into the Hind III site at nucleotide 162 (FIG. 2) was not detected by the transcription and amplification assay of the present invention merely indicates that packaging of DI RNA molecules having inserted therein CAT RNA sequences was not detected. Replication and/or expression may indeed have occurred in the transfected cells. Additionally, other heterologous RNA sequences which do not interfere with the possibly required RNA structure provided by the first 162 nucleotides of the DI RNA molecule may be efficiently replicated and packaged. Furthermore, it may be possible to remove the structural interference caused by the CAT sequences employed in the present invention by substituting various nucleotides by methods known to those skilled in the art (e.g. consistent with the degeneracy of the genetic code) while still encoding a functional CAT protein. Thus, the present invention provides for cloning and/or expression vectors comprising nucleotides 1 to about 241 and nucleotides from about 1928 to at least 2314, followed by a poly A tail, which permit replication and packaging of heterologous nucleic acid inserted therein.

Furthermore, by techniques known to those skilled in the art, any other heterologous nucleic acid may similarly be inserted at the BalI restriction endonuclease site in the DI cDNA. Given the broad host range of alphaviruses, generally, and Sindbis virus, specifically, heterologous sequences may thus be specifically chosen to correspond with a specific host cell so as to provide the desired processing (e.g. glycosylation) specific to the chosen host cell. In accordance with the known requirements of RNA translation in eucaryotic host cells, the heterologous nucleic acid inserted into a DI vector of the present invention should contain a translation start-signal codon immediately preceding the sequence to be translated, a sequence encoding the protein or protein fragment to be made in the host cell followed by a translation termination codon. A sequence encoding the poly A tail of the heterologous RNA to be translated will be derived from the DI RNA.

Also of significance is our finding that the RNA sequences required for replication and packaging of the Sindbis virus DI RNA molecule of the present invention constitute highly conserved sequences shared by such other alphavirus studied to date, Ou (1982) (1983) (1984), as Ross River, Middleburg, and Semliki Forest viruses. (Lehtovaara et al. (1982); Monroe et al. (1982). The conservation of these sequences suggests that the DI RNA sequences of the present invention (e.g. nucleotides 1 to 241 and 1928 to at least 2314, followed by a poly A tail) or variants thereof may be employed directly and/or as alternative sequences in the construction of DI RNA vectors which permit replication and packaging of heterologous RNA inserted therein in the presence of Ross River, Middleburg, and/or Semliki Forest virus. The term "variants" when applied to the sequences of the present invention required to effect replication and packaging of DI RNA in the presence of helper virus is herein understood to comprise any nucleotide deletions, substitutions, additions and/or inversions which do not interfere with the ability of the described sequences to permit DI RNA replication and packaging in the presence of helper virus or helper cells assayable in the transfection and replication assay of the present invention.

Furthermore, by employing, the herein described transfection and amplification assay to screen deletions in other alphavirus cDNAs alone and/or in conjunction with the comparative screening of specific alphaviruses for RNA regions essentially homologous to nucleotides 1 to 241 and 1928 to at least 2314, followed by a poly A tail (FIG. 1), RNA vectors may be constructed by analogous methods known to those skilled in the art which vectors are capable of effecting the replication and packaging of heterologous RNA inserted therein.

Microorganisms and Plasmids

The following microorganism is available from the American Type Culture Collection (ATCC), 12301 Parklawn Drive, Rockville, Md., 20852, U.S.A.:

ATCC 53426—*E. coli* MC1061 (plasmid KDI-25)

EXAMPLE 1

All restriction enzymes and DNA modifying enzymes were obtained from New England Biolabs (Beverly, Mass.), Boehringer Mannheim Biochemicals (Indianapolis, Ind.), Pharmacia-PL Biochemicals (Piscataway, N.J.) and Bethesda Research Laboratories (Gaithersburg, Md.) and used in accordance with manufacturers' instructions. All general recombinant DNA techniques such as DNA ligations, transfections, transformations, restriction endonuclease fragment isolations etc. were performed in accordance with the methods described in Maniatis et al. (1982) unless otherwise specified. Radio-labeled nucleotides were obtained from Amersham (Arlington Heights, Ill.).

Synthetic DNA multilinkers and/or fragments used to construct certain of the plasmids were assembled on an Applied Biosystems DNA Synthesizer (Applied Biosystems, Inc., Foster City, Calif.) following the manufacturer's recommended procedures.

Assays for chloramphenicol acetyl transferase (CAT) were carried out as described by Fromm et al. (1985).

EXAMPLE 2

This example demonstrates the transcription of plasmid DNA comprising the SP6 bacteriophage promoter and DI cDNA. This example further demonstrates the transfection of chick embryo fibroblasts with DI RNA transcripts obtained from the in vitro transcription of plasmid DNA comprising the SP6 bacteriophage promoter and DI cDNA. The herein described transcription and transfection assays were used to analyze all RNAs.

Briefly, plasmid DNAs were linearized at the unique PstI site (FIG. 2) in preparation for transcription. Between 1 and 3 $\mu$g of plasmid were incubated for 30 to 60 minutes at 41° C. with SP6 polymerase following the conditions described by the supplier or by Melton et al. (1984). The SP6 polymerase may be obtained from New England Biolabs, Inc. (Beverly, Mass.). The reactions were stopped by the addition of phenol/chloroform and the nucleic acid extracted as described by Maniatis et al. (1982).

For transfection, monolayers of secondary chicken embryo fibroblasts were treated for 20 to 60 minutes (min) with 20 $\mu$g per ml DEAE dextran in minimal essential medium buffered with Tris HCl to pH 7.5. Al-Moslih and Dubes (1973). After removal of the DEAE dextran, varying concentrations of transcribed DI RNA and infectious Sindbis virus, at a multiplicity of 20 to 50, were added to the cells for one hour (h). Essentially all of the cells received helper virus and some fraction also received the transcribed DI RNA. After this time the inoculum was removed and minimal essential medium containing 3% chicken serum was added to the dishes (2 ml/60 mm dish). Most transfection assays were carried out in 60 mm dishes containing $3 \times 10^6$ cells. The infected cells were incubated for 12 to 16 h at 37° C. at which time the medium was harvested. This harvest was designated passage one. One-fourth of the sample was used to infect new monolayers of chicken embryo fibroblasts which were incubated for 10–14 hours before harvesting the medium (passage two). Cells were routinely assayed during the formation of passage 3 for the presence of DI RNA which became the predominant viral RNA species in those cells transfected with DI RNA. The level of amplification of transcribed DI-25 RNA and of the naturally-occurring DI-2 was similar. DI-25 RNA could be detected in cells during the formation of passage 2 when 100 ng or more of RNA was used for transfection. When cells were transfected with 1 ng of DI-25 RNA, however, the amplified RNA was not detected until passage 3.

As shown in Table 1, below, when employing the transfection and amplification assay of the present invention, the only cells that contained RNA, (e.g. RNA of less than 26S in size) were those cells that had been transfected with intact RNA. DI RNAs were not detected in those cells that were mock-transfected and infected with helper virus. Furthermore the appearance of DI RNA was dependent on transcription. Treatment of the plasmid with DNase before transcription prevented the appearance of the DI RNA; after transcription the appearance of the RNA was sensitive to RNase, but not to DNase. Additionally, amplification of the DI RNA was monitored both by the appearance of DI RNA and by a drop in the yield of infectious virus. Also shown in Table 1, below, is that the detection of the defective RNA was correlated with a decrease in plaque-forming virus released into the medium of the infected cells.

Analysis of the DI-25 RNA transcripts in accordance with the methods described above indicated that the DI-25 RNA transcripts differed from naturally-occurring DI RNAs in several ways. Specifically, the transcribed RNA (e.g. DI-25 RNA) was not capped and contained two extra Gs at the 5' terminus as a result of cloning. The DI-25 RNAs also contained 19 Cs following the poly A stretch at the 3' end as well as 4 nucleotides of the polylinker region into which the DI cDNA had been inserted (FIG. 4). None of these differences, however, prevented the replication and amplification of the transcribed DI RNA.

In the experiments described below DI RNAs with specific deletions were tested for their ability to be amplified after transfection into chicken embryo fibroblasts. In those cases in which DI RNA was not detected in cells during the formation of passage 3, an additional passage was also analyzed.

TABLE 1

Transcription and Transfection Conditions Required for the Amplification of DI RNA

| Transcription or Transfection Condition | Intracellular DI-25 RNA detected at passage 3 | Virus Yield at Passage 3 (PFU × 10⁻⁹) |
|---|---|---|
| 1. Transcription reaction | | |
| All components present | + | 0.17 |
| SP6 polymerase | − | 14 |
| ribonucleotide triphosphates | − | 11 |
| DNase I added before SP6 polymerase* | − | 13 |
| DNase I added after completion of transcription* | + | 0.14 |
| RNase added after completion of transcription* | − | 11 |
| 2. Transfection and passaging | | |
| + he per virus alone | − | 19 |
| − he per virus | − | 0 |

*The samples were treated with either DNase I (50 μg per μl) or RNase A (100 μg/μl) for 15 min at 37° C.

EXAMPLE 3

The following example demonstrates the construction of bacterial plasmid KDI-25 which comprises the SP6 promoter and a complete cDNA of an alphavirus DI RNA genome. E. coli strain MC1061 containing plasmid KDI-25 has been deposited with the American Type Culture Collection (Rockville, Md.) and has been given ATCC accession number 53426.

The construction of plasmid pSS01 and isolation of Sindbis virus DI-2 RNA is described by Monroe and Schlesinger (1984). The original cDNA clone (pSS01) of DI-2 RNA lacks the 28 5' terminal nucleotides of the naturally-occurring DI-2 RNA.

Monroe and Schlesinger (1984). The procedures for extending the 5' terminus and positioning it directly downstream from the SP6 promoter are described in FIG. 4. The DNA was digested with HpaII and a 264 base pair (bp) fragment extending from position 38 to 301 was isolated for use as primer. This fragment was annealed to DI-2 RNA and extended by reverse transcription to obtain a full length 302 nucleotide product. This single-stranded DNA was isolated by gel purification and tailed with dCTP using terminal transferase. The general strategy of Okayama and Berg (1982) was used in the synthesis of the second strand. As a primer we used a G-tailed SacI to HphI 251 bp linker fragment containing the SP6 promoter derived from plasmid K11. The plasmid K11 was obtained from Dr. Henry Huang, Department of Microbiology and Immunology, Washington University, St. Louis, Mo. Alternatively, the SP6 promoter sequence may be obtained from Promega-Biotech (Madison, Wis.) or Bethesda Research Laboratories (Gaithersburg, Md.). The SP6 promoter is indicated by the darkened area directly upstream from the HphI site on the primer-linker fragment (FIG. 4). This fragment contains a 249 nucleotide sequence identical to that published by Melton et al. (1984) for the SP6 promoter in the SP6 cloning vector pSP64 beginning at position −248 from the first G (designated +1). This is the nucleotide at which the polymerase initiates transcription in pSP64. In our 251 bp fragment the SacI site lies 2 nucleotides upstream from position −248 and the HphI restriction site is directly after the G designated +1 in the pSP64 published sequence. Melton et al. (1984). Thus, the start site for the SP6 polymerase is located at this G preceding the HphI cut site. After extension, the fragment was cleaved with HindIII and the resulting SacI/HindIII fragment was ligated to a SacI/HindIII cut 4078 bp fragment derived from the intermediate hybrid clone (KSS01) as indicated in FIG. 4. KSS01 contains 2292 bp derived from an EcoRI/HindIII fragment of K11 and 2216 bp derived from a HindIII/EcoRI fragment of pSS01. The latter plasmid contains DI-2 sequences, including 21 A/Ts, followed by 19 C/Gs and a 27 bp polylinker derived from PUC4, Monroe and Schlesinger, (1984). The plasmid designated KDI-2 in FIG. 4 contains the complete sequence of DI-2 cDNA downstream from the SP6 promoter and separated from the transcription start site by a stretch of G/C base pairs. To bring the DI cDNA sequence to a position directly downstream from the SP6 promoter, a 21 bp oligonucleotide of the following sequence:

5'-GATATAGTGGTGAGTATCCCC-3'
CCTATATCACCACTCATAGGG was synthesized. The top line of this sequence corresponds to the first 20 nucleotides at the 5' terminus of DI-2 (plus an extra terminal 5'G). This oligonucleotide was substituted into the plasmid between 2 HphI restriction sites (one located at the +1 position beyond the SP6 polymerase start site and the other 20 nucleotides from the true 5' terminus of the DI-2 cDNA sequence) in place of the original HphI fragment containing the long G/C stretch (FIG. 4). The junction sequence -GGTGACACTATAGGATATAGTGGT GA- was determined by sequence analysis. Maxam and Gilbert (1980). The HphI recognition sequence (8 nucleotides upstream from the restriction site) and the two Gs ending the SP6 polymerase promoter and starting the 21 mer are underlined. The final clone was designated KDI-25.

A clone containing the 5' terminal sequences of virion 49S RNA directly downstream from the SP6 promoter was similarly constructed. The SacI/HindIII fragment from this plasmid was inserted into KDI-25 in place of the SacI/HindIII fragment described in FIG. 4.

EXAMPLE 4

This example demonstrates the construction of various deletions in the Sindbis virus DI cDNA sequence. The RNA's transcribed from the DI cDNA's carrying the deletions described in this example 4 were then assayed for their respective abilities to replicate and become packaged in the presence of helper virus.

a. 3' Terminus Deletions

Starting at nucleotide 2248, downstream deletions of 25, 41, 42, 48, 50, 53 and 54 nucleotides were made. Construction of the 3' terminal deletions was performed as follows. KDI-25 was digested with NaeI, see FIG. 2 and then with Bal31 for variable lengths of time. The DNA samples were treated with DNA polymerase large fragment (Klenow) and then analyzed by digestion with HhaI. One of the restriction sites of HhaI is 253 bp downstream from the NaeI site at nucleotide 2247. A double digestion with HhaI and NaeI permitted the identification of those fragments with deletions in the desired size range. See Table 2, below. The DNA plasmids to be investigated further were digested with BglI which has a single site at nucleotide 3274 in the vector region of KDI-25 (FIG. 2). Bal31/BglI fragments ranging in size from 962 to 1022 bp were cloned into a BglI/NaeI fragment obtained by partial digestion with NaeI to generate the fragment cleaved with NaeI at nucleotide 2247 (see FIG. 2). The exact deletions made by the Bal31 digestion were determined by sequencing the purified plasmid DNAs in the region covering the 3' terminus of the DI RNA. Oligo(dT)$_{12}$GA was used as primer on denatured double-stranded template, McGraw (1984), and sequencing was carried out by the dideoxy chain termination method described by Sanger et al. (1977).

Digestion with Bal31 produced a deletion that retained the nineteen nucleotide conserved region (KDI-348) and clones KDI-353 and KDI-354 in which 5 and 6 nucleotides had been removed, respectively, from that region. The 18th and 19th nucleotides from the 3' terminus were deleted by site specific mutagenesis. A HindIII/EcoRI fragment from KDI-348 was inserted into the RF of M13. (The EcoRI site is at site 2375, 17 nucleotides downstream from the PstI site, FIG. 2). Specific M13 cloning vectors may be obtained from New England Biolabs (Beverly, Mass.) or Bethesda Research Laboratory, Inc. (Gaithersburg, Md.). Site-specific mutagenesis was carried out using the synthetic oligonucleotide 5'TGTCAGCCTTTGTTTT3' which was the same sense as the DI RNA and complementary to the single-stranded M13 DNA. The two nucleotides underlined are the nucleotides on either side of the two deleted nucleotides. The mutagenesis and selection procedures were those described by Kunkel (1985) using the E. coli dut-, ung- strain. The mutagenized phage were detected by colony hybridization, Thayer (1979), using the synthetic oligonucleotide as probe and by sequencing using oligo (dT)$_{12}$GA as primer. After establishing that the DNA in M13 had the correct deletion, we isolated a NaeI/PstI fragment from the RF and cloned it into the NaeI (site 1340)/PstI vector derived from KDI-348. The deletion of the two nucleotides was confirmed by sequencing the plasmid DNA using the dideoxy chain termination method as described above.

TABLE 2

| Plasmid Designation | Sequence | Interference* |
|---|---|---|
| KDI-25 | NaeI | 0.05 |
| | CAGCCGGCCGCTCATGCAGACTACTTTTATTATTTC | |
| | TTTTATTAATCAACAAA<u>ATTTTGTTTTTAACATTTC</u> | |
| KDI-325 | CAGCC TATTTCTTTTATTAATCAACAAAATTTTGTTTTTAACATTTC | 0.12 |
| KDI-341 | CAGCC CAACAAAATTTTGTTTTTAACATTTC | 0.17 |
| KDI-342 | CAGCC AACAAAATTTTGTTTTTAACATTTC | 0.06 |
| KDI-348 | CAGCC ATTTTGTTTTTAACATTTC | 0.08 |
| KDI-350 | CAGCC TTTGTTTTTAACATTTC | 1.0 |
| KDI-353 | CAGCC GTTTTTAACATTTC | 0.9 |
| KDI-354 | CAGCC TTTTTAACATTTC | 1.1 |

*Chicken embryo fibroblasts were transfected with RNA transcribed from the designated plasmid and infected with helper virus, or were infected with helper virus alone.
Interference is defined as the virus yield at the third passage after transfection and infection divided by the yield of virus after infection with helper virus alone.
The 19 conserved nucleotides at the 3' terminus are underlined.

As shown by the results presented in Table 2 above, deletions of 48 nucleotides or less did not effect the ability of the DI RNA to be amplified. The deletion of 48 nucleotides left intact the nineteen nucleotides at the 3' terminus. Extensions into the 19 nucleotide 3' sequence, even by two nucleotides, inactivated the DI RNA transcript. This conclusion was based on the absence of any DI RNA in the infected cells after either three or four passages and on the lack of any interference in the replication of infections virus measured by virus titer (Table 2).

b. Internal Deletions

The internal region of DI-25 was defined to be from nucleotide 241 (the BalI site) to nucleotide 2247 (the 3'

NaeI site). The specific deletions and plasmid designations are described and listed, respectively, in Table 3, below (See also FIG. 3).

Construction of the internal deletions was similarly performed as follows. The plasmid designations are listed in Table 3. KDI-1701 was obtained by partial digestions with BalI and NdeI. The deletions in KDI-103 and KDI-107 were generated by NdeI and NaeI digestions, respectively (see FIG. 2). The deletion in KDI-1320 was obtained by partial digestion with MspI. KDI-131 was constructed making use of the BalI site at 241 and the MspI site at 619. The plasmids were analyzed with appropriate restriction enzymes to establish that the deletions were as indicated. RNA transcribed from each of the deleted clones was amplified after transfection and the DI particles produced interfered with the yield of helper virus as shown in Table 3, below. Thus, none of these internal sequences were required for the viability (e.g. replication and packaging) of the DI RNA.

TABLE 3

Description of Plasmids with Internal Deletions in KDI-25

| Plasmid designation | Deleted region | Size of DI RNA transcript (nt) | Interference |
|---|---|---|---|
| KDI-1701 | 242–1152 | 1448 | 0.07 |
| KDI-131 | 242–620 | 1980 | 0.003 |
| KDI-1320 | 307–717 | 1948 | 0.006 |
| KDI-103 | 1153–2059 | 1452 | .04 |
| KDI-107 | 1341–2247 | 1452 | .02 |

Chicken embryo fibroblasts were transfected with RNA transcribed from the designated plasmid and infected with helper virus, or were infected with helper virus alone. Interference is defined as the virus yield at the third passage after transfection and infection divided by the yield of virus after infection with helper virus alone.

The transcribed RNAs were considerably smaller than either naturally-occurring DI RNAs or the other DI RNAs obtained from cDNA clones. These small DI RNAs (60 to 80% the length of DI-25 RNA) evolved rapidly during passaging. In some cases by the third passage the original DI RNAs had been almost completely replaced by larger DI RNAs. The DI RNAs amplified from transcripts 103 and 107 were analyzed in more detail to determine if those RNA species migrating at the same position as the original transcripts actually retained the original sequences. Viral RNAs, labeled with [$^{32}$Pi] during synthesis were hybridized to the appropriate plasmid DNA, digested with nuclease S1 and then analyzed by agarose gel electrophoresis. The original transcripts and those DI RNAs of the same size were protected from digestion by S1. In contrast, the other species in the preparation were digested as were 26S and 49S RNA.

c. 5' Terminal Deletions

The 5' terminal deletions were constructed in a manner similar to the constructions of the 3' terminal and internal deletions. The 5' terminal deletions constructed are summarized in FIG. 3. Briefly, the studies of Ou et al. (1983) identified two regions at the 5' terminus of the alphavirus genome that are conserved among alphaviruses. One of these is the exact 5' terminus and the other is the 51 nucleotide region extending from nucleotides 155 to 205 in the Sindbis genome and from nucleotides 193 to 243 in DI-25. The latter region shows a very high degree of conservation among alphaviruses and is retained in all of the DI RNAs so far examined. Lehtovaara et al. (1982); Monroe and Schlesinger (1984). To determine if this sequence is essential for the biological activity of DI RNAs we deleted it from KDI-25. The sequences removed extended from the HindIII site at nucleotide 162 to the BalI site at 241 (FIG. 2). RNA transcribed from this plasmid (KDI-554) was amplified in the transfection and passaging assay with what appeared to be the same efficiency as the prototype DI-25 RNA. This result was unexpected and the DI RNA isolated from the infected cells was analyzed in more detail to determine if this nucleotide sequence was still deleted after amplification. We sequenced the relevant region of the RNA using an oligonucleotide primer complementary to nucleotides 285 to 300 in KDI-25 RNA to make a cDNA copy. The cDNA was sequenced by the method of Maxam and Gilbert (1980) and the sequence obtained was that expected for the cloning events which joined the HindIII/BalI sites.

In addition, we established by blot hybridization that the 51 nucleotide region had not been inserted in another region of the RNA. The probe to detect the deleted region was an oligonucleotide extending from nucleotides 168 to 184. Tsiang et al. (1985). (The total deletion extends from nucleotides 163 to 240.) DI-554 RNA isolated from the third passage was not detected with this probe, which did hybridize to DI-25 RNA. The RNA not detected by this first probe was recognized by a probe from another region of the genome.

We considered the possibility that the tRNA$^{Asp}$ sequences at the 5' end of these DI RNAs might, in some way, obviate the requirement for the 51 nucleotide sequence. DI-25 contains nucleotides 10-75 of tRNA$^{Asp}$ at the 5' terminus. The CCA 3' terminus of the tRNA is joined to the viral sequences at nucleotide 31 of the virion RNA. Monroe and Schlesinger (1983). We replaced the tRNA$^{Asp}$ sequences with the 5' terminal sequences of the virion RNA. The RNA transcribed from this plasmid was biologically-active. Again, deletion of the region from the HindIII site to the BalI site did not affect the ability of this RNA to be replicated and packaged.

The 5' terminal 40 nucleotides is the least conserved among the four regions defined by Ou et al. (1983). Furthermore, analysis of the 5' termini of six different Sindbis DI RNAs shows extensive variations in this region. Although the most common 5' terminus is that of tRNA$^{Asp}$, one DI RNA actually contains sequences from the 5' terminus of 26S RNA. Tsiang et al. (1985).

Several clones containing deletions at the 5' terminus arose during the cloning of KDI-25. The exact number of nucleotides deleted was established by sequencing. One clone (KDI-507), see FIG. 3, lacked nucleotides 1 through 7 at the 5' terminus and one (KDI-514) had a deletion extending from nucleotides 22 to 162. RNA transcribed from these clones was not detected upon passaging after transfection. As described earlier, in the cases in which DI RNA was not detected in infected cells by passage 3, an additional passage was analyzed. Thus, it was determined that at least nucleotides 1 to about 162, FIG. 1, at the 5' terminus were essential for DI RNA viability in the transfection and amplification assay of the present invention.

EXAMPLE 5

Figure 5:
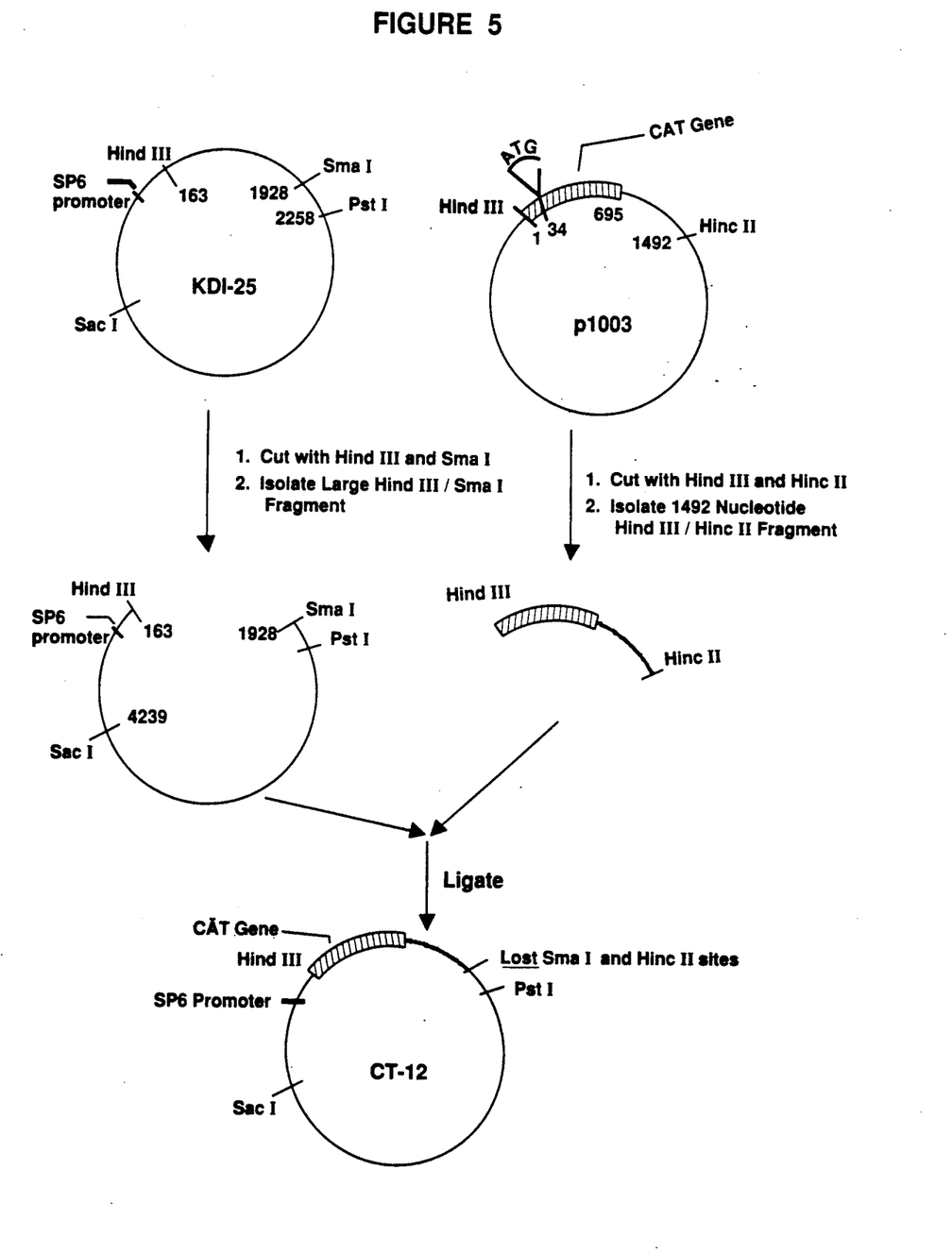
FIG. 5 depicts the construction of plasmid CT-12 comprising plasmid KDI-25 having inserted therein at the Hind III restriction endonuclease site a fragment comprising DNA encoding the *E. coli* chloramphenicol acetyl transferase enzyme (CAT Gene denoted by the hatched region) and various SV40 and bacterial plasmid sequences (denoted by the squiggly line). The numbers in KDI-25 denote nucleotide positions wherein number 1 was assigned to the first nucleotide of the DI-25 cDNA (see FIG. 1). The numbers in p1003 denote nucleotide positions wherein number 1 was assigned to the first nucleotide in the CAT gene-containing fragment inserted into KDI-25. The translation start-signal codon (ATG) for the CAT gene begins at nucleotide 34 in P1003.
Figure 6:
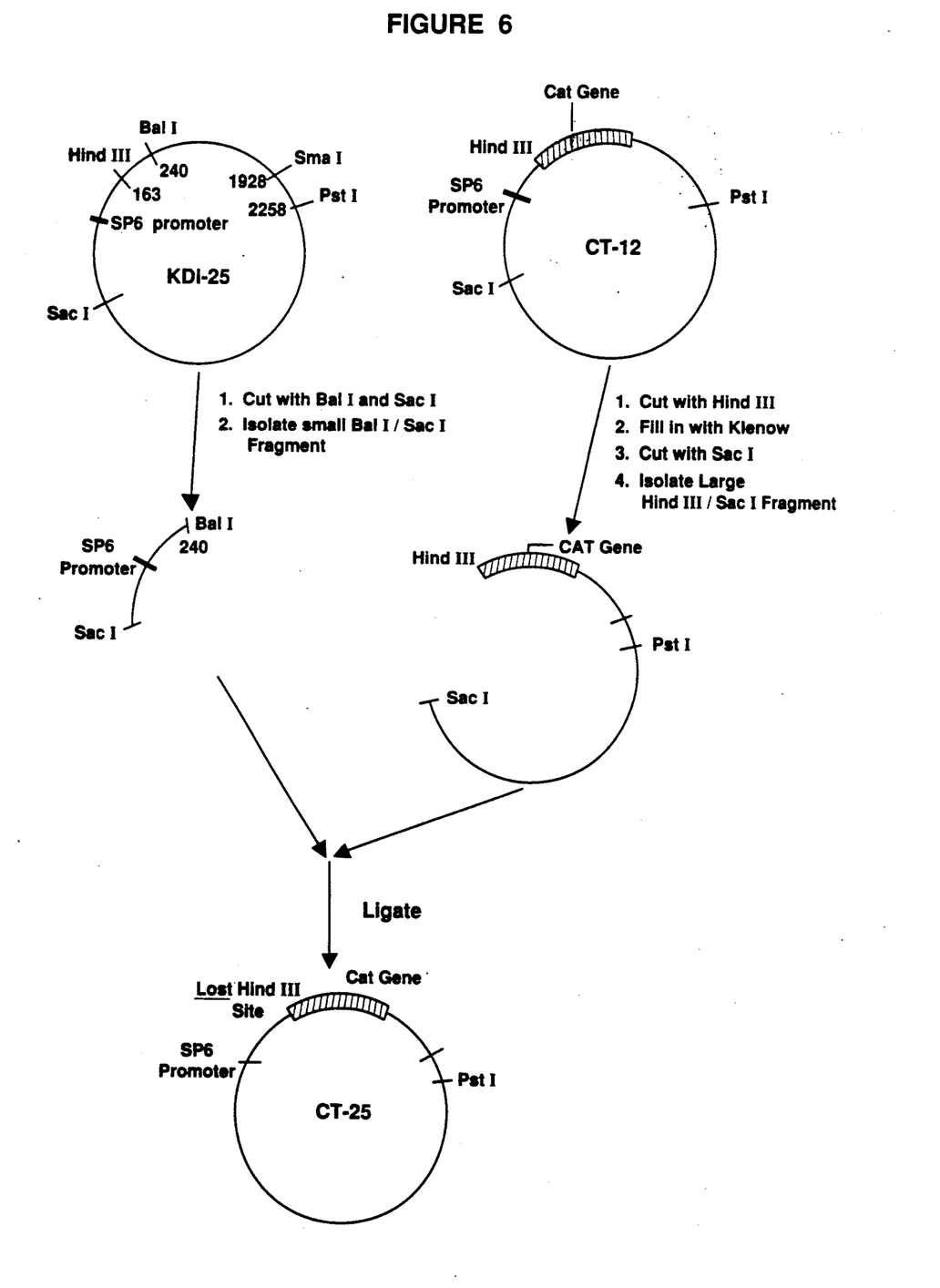
FIG. 6 depicts the construction of plasmid CT-25 comprising plasmid KDI-25 having inserted therein at the Bal I restriction endonuclease site a fragment comprising DNA encoding the bacterial CAT enzyme (denoted by the hatched region and labeled "CAT Gene") and various SV40 and bacterial plasmid sequences (denoted by the squiggly line). The numbers denote specific nucleotides in the DI-25 cDNA (see FIG. 1).

The following example demonstrates the construction of an alphavirus vector comprising Sindbis virus DI RNA having inserted therein heterologous RNA. Briefly, DNA sequences encoding the E. coli chloramphenicol acetyl transferase (CAT) protein were inserted into DI-25 cDNA at the BalI site (FIGS. 5 and 6). RNA transcripts of the DI-25 cDNA containing the CAT coding sequences were made in vitro employing the SP6 polymerase as previously described. The RNA transcripts comprising DI-25 RNA having inserted therein RNA encoding the CAT protein were then employed to transfect CEFs in the presence of helper Sindbis virus as previously described. After one or two passages, transformed CEFs were assayed for the presence of CAT activity following the procedures described by Fromm et al. (1985). Additionally, intracellular RNA and RNA derived from infectious Sindbis virus particles were analyzed as previously described to demonstrate the presence in infected cells and virus particle of DI RNA having inserted therein RNA encoding the CAT protein.

Specifically, as shown in FIG. 5, the DNA sequences (gene) encoding the CAT protein were isolated from plasmid p1003 which was obtained from Dr. John Majors, Department of Biochemistry, Washington University (St. Louis, Mo.). DNA sequences encoding the CAT protein may also be obtained from *E. coli* plasmid pBR325 or can be chemically synthesized. The CAT gene was isolated from p1003 as a 1492 nucleotide fragment by digestion of said plasmid with Hind III and Hinc II and inserted into KDI-25 which had been previously digested with Hind III and Sma I. The 1492 nucleotide Hind III/Hinc II fragment was then ligated into the restriction digested KDI-25 plasmid to create plasmid CT-12 shown in FIG. 5. As shown in FIG. 6, insertion of the CAT gene into the Bal I site of the DI-25 cDNA was achieved as follows. Plasmid CT-12 was digested with Hind III and the Hind III site filled-in with *E. coli* DNA dependent DNA polymerase (Klenow fragment), then cut with SacI and the large plasmid fragment isolated. The small BalI to SacI fragment of KDI-25 previously cleaved with BalI and SacI was then ligated to the isolated HindIII/SacI fragment of CT-12. The resultant plasmid was designated CT-25 (FIG. 6).

Approximately one μg of transcript RNA obtained by the in vitro transcription of linearized CT-25 performed as previously described was employed to transfect CEFs in the presence of standard Sindbis virus at a multiplicity of infection of 50. After one to two passages CAT enzyme activity was detected in transfected and infected CEFs indicating expression of the CAT RNA carried on the DI-25 RNA. Additionally, infectious virus particles comprising DI-25 RNA having inserted therein CAT RNA sequences were isolated demonstrating the replication and packaging of the chimeric (e.g. DI-25 RNA containing CAT RNA) RNA. As the CAT-containing fragment inserted into DI-25 RNA also comprised SV40 and bacterial sequences, the present example demonstrates the replication and packaging of at least three different heterologous nucleic acids, for a total size being at least 1492 nucleotides in length, employing the vectors of the present invention.

REFERENCES

Al-Moslih, M. I. and Dubes, G. R. (1973) *J. Gen. Virol.* 18: 189–193.

Ashman, C. R. and Davidson, R. L. (1984) *Mol. Cell Biol.* 4: 2266–2272.

Bras-Herreng, F. (1975) *Arch. Virol.* 48: 121–129.

Bras-Herreng, F. (1976) *Ann. Microbiol.* (Paris) 127b: 541–565.

Carlos, M. P., Lebkowski, J. S., Botcham, M. R. (1983) *Proc. Nat'l Acad. Sci. U.S.A.* 80: 3015–3019.

Clark, H. F., Cohen, M. M., Lunger, P. D. (1973) *J. Nat'l. Cancer Inst.* 51: 645–654.

Fromm, M., Taylor, L. P. and Walbot, V. (1985) *Proc. Nat'l Acad. Sci., U.S.A.* 82: 5824–5828.

Guild, G. M. and Stollar, V. (1977) *Virology* 77: 175–188.

Kääriäinen, L., R. F. Pettersson, S. Keränen, P. Lehtovaara, H Söderlund, and P. Ukkonen (1981) *Virology* 113:686–697.

Kamen, Robert I., (1975) in "RNA Phages" ed. Zinder, Cold Spring Harbor, N.Y.

Kunkel, T. A. (1985) *Proc. Nat'l. Acad. Sci., U.S.A.* 82:488–492.

Lehtovaara, P., Söderlund, H., Keränen, S., Pettersson, R. F. and Kääriäinen, L. (1982) *J. Mol. Biol.* 156: 731–748.

Maniatis, T., Fritsch, E. F. and Sambrook, J. eds. (1982) "Molecular Cloning, A Laboratory Manual", Cold Spring Harbor Laboratories, Cold Spring Harbor, N.Y.

Maxam, A. M. and Gilber, W. (1980) *Meth. Enzymol.* 65: 499–560.

McGraw III, R. A. (1984) *Anal. Biochem.* 143:298–303.

Melton, D. A., Krieg, P. A., Rebagliati, M. R., Manaitis, T., Zinn, K. and Green, M. R. (1984) *Nucleic Acids Res.* 12: 7035–7056.

Monroe, S. S. and Schlesinger, S. (1983) *Proc. Nat'l Acad. Sci., U.S.A.* 80: 3279–3283.

Monroe, S. S. and Schlesinger, S. (1984) *J. Virol.* 49: 865–872.

Monroe, S. S., Ou, J. H., Rice, C. M., Schlesinger, S., Strauss, E. G. and Strauss, J. H. (1982) *J. Virol.* 41: 153–162.

Okayama H. and Berg, P. (1982) *Mol. Cell. Biol.* 2: 161–170.

Ou et al. (1981) *Virology* 109: 281–289.

Ou et al. (1982) *Proc. Nat'l. Acad. Sci.* 79: 5235–5239.

Ou et al. (1983) *J. Mol. Biol.* 168: 1–15.

Perrault, J. (1981) *Curr. Top. Microbiol. Immunol.* 93: 151–207.

Pettersson, R. F. (1981) *Proc. Nat'l. Acad. Sci., U.S.A.* 78: 115.

Rigby, P. W. J. (1983) *J. Gen. Virol.* 64: 255–266.

Sanger, F., Nicklen, S. and Coulson, A. R. (1977) *Proc. Nat'l. Acad. Sci., U.S.A.* 74: 5463–5467.

Schlesinger, R. ed. "The Togaviruses, Biology, Structure and Replication", Academic Press, New York, N.Y.

Stark, C. and Kennedy, S. I. T. (1978) *Virology* 89: 285–299.

Thayer, R. E. (1979) *Anal. Biochem.* 98: 60–63.

Tsaing, M., Monroe, S. S. and Schlesinger, S. (1985) *J. Virol.* 54: 38–44. Weiss, B., Rosenthal, R. and Schlesinger, S. (1980) *J. Virol.* 33: 463–474.

What is claimed is:

1. A RNA vector consisting essentially of, in sequence, Sindbis virus DI RNA nucleotides 1 to 241, an RNA sequence complementary to a restriction endonuclease site, and Sindbis virus DI RNA nucleotides 1928 to 2314, followed by a poly A tail.

2. The vector of claim 1 additionally comprising a heterologous RNA sequence complementary to a DNA sequence inserted at the restriction site.

3. Essentially pure Sindbis virus DI RNA consisting essentially of nucleotides 1 to 241 and 1928 to 2314, followed by a poly A tail.

4. An expression vector consisting essentially of, in sequence, Sindbis virus DI RNA nucleotides 1 to 241, heterologous RNA comprising a translation start-signal codon followed by RNA sequences encoding a protein or fragment thereof to be expressed, followed by a translation termination codon, and Sindbis virus DI RNA nucleotides 1928 to 2314, followed by a poly A tail.

5. A genetically altered eucaryotic cell containing RNA consisting essentially of, in sequence, Sindbis virus DI RNA nucleotides 1 to 241, heterologous RNA comprising a translation start-signal codon followed by RNA-sequences encoding a protein or fragment thereof to be expressed, followed by a translation termination codon, and Sindbis virus DI RNA nucleotides 1928 to 2314, followed by a poly A tail.

6. A genetically altered Sindbis virus DI particle containing RNA consisting essentially of, in sequence, Sindbis virus DI RNA nucleotides 1 to 241, heterologous RNA comprising a translation start-signal codon, followed by RNA-sequences encoding a protein or fragment thereof to be expressed, followed by a translation termination codon, and Sindbis virus DI RNA nucleotides 1928 to 2314, followed by a poly A tail.

7. A method of replicating heterologous RNA in eucaryotic cells comprising the steps of:
   a. cloning a first DNA molecule comprising a cDNA of a Sindbis virus DI RNA molecule downstream from a promoter able to cause transcription by a DNA dependent RNA polymerase;
   b. substituting into the Sindbis virus cDNA a second DNA molecule comprising a heterologous DNA between nucleotides 241 and 1928 to create a chimeric DNA;
   c. transcribing the chimeric DNA into chimeric RNA;
   d. transfecting the eucaryotic cell with the chimeric RNA in the presence of helper virus; and
   e. growing the transfected eucaryotic cells under conditions which promote replication of Sindbis virus DI RNA.

8. A method of replicating a heterologous RNA in a eucaryotic cell comprising the steps of:
   a. isolating plasmid KDI-25 from an *E. coli* culture having ATCC accession number 53426;
   b. inserting heterologous DNA into the BalI site of plasmid KDI-25 to create a chimeric plasmid,
   c. transcribing the chimeric plasmid, into chimeric RNA;
   d. transfecting a eucaryotic cell with the chimeric RNA in the presence of helper virus; and
   e. growing the transfected eucaryotic cells under conditions which promote the replication of Sindbis virus DI RNA.

9. A method of preparing a vector consisting essentially of, in sequence, Sindbis virus DI RNA nucleotides 1 to 241, heterologous RNA, and Sindbis virus DI RNA nucleotides 1928 to 2314, followed by a poly A tail, the method comprising the steps of:
   a. cloning a first DNA molecule comprising a cDNA of a Sindbis virus RNA molecule downstream from a promoter able to cause transcription by a DNA dependent RNA polymerase;
   b. substituting into the Sindbis virus cDNA a second DNA molecule comprising DNA encoding heterologous protein between nucleotides 241 to 1928 to create a chimeric DNA molecule;
   c. transcribing the chimeric DNA molecule into a chimeric RNA molecule; and
   d. isolating the chimeric RNA molecule.

10. A method of producing a heterologous protein in a eucaryotic cell comprising the steps of:
    a. cloning a first DNA molecule comprising a cDNA of a Sindbis virus DI RNA downstream from a promoter able to cause transcription by a DNA dependent RNA polymerase;
    b. substituting into the Sindbis virus cDNA a second DNA molecule comprising DNA sequences encoding the heterologous protein between nucleotides 241 and 1928;
    c. transcribing the first DNA and the second DNA contained therein as a continuous transcript;
    d. transfecting a eucaryotic cell with the continuous transcript in the presence of helper virus; and
    e. growing the transfected eucaryotic cell under conditions which provide for the expression of Sindbis virus DI RNA.

11. A method of producing heterologous protein in a eucaryotic cell which comprises expression of RNA, said RNA consisting essentially of, in sequence, Sindbis virus DI RNA nucleotides 1 to 241, heterologous RNA comprising a translation start-signal codon, followed by sequences encoding the heterologous protein to be produced in said cell, followed by a translation stop-signal codon and Sindbis virus DI RNA nucleotides 1928 to 2314, followed by a poly A tail, and recovering the resulting heterologous protein produced within said eucaryotic cell.

12. Plasmid KDI-25 having ATCC accession number 53426.

13. A method for genetically modifying a Sindbis virus comprising the steps of:
    a. Cloning a first DNA molecule comprising a cDNA of a Sindbis virus DI RNA molecule downstream from a promoter able to cause transcription by a DNA dependent RNA polymerase;
    b. substituting into the Sindbis virus cDNA a second DNA molecule comprising heterologous DNA between nucleotides 241 and 1928;
    c. transcribing the first and second DNA molecules as a continuous transcript;
    d. transfecting a host cell with the continuous transcript in the presence of helper virus; and
    e. isolating Sindbis DI particles comprising Sindbis DI RNA having inserted therein heterologous RNA.

14. An infectious Sindbis defective interfering (DI) alphavirus particle containing RNA consisting essentially of, in sequence, Sindbis virus DI RNA nucleotides 1 to 241, at least one protein coding sequence from a heterologous gene and Sindbis virus DI RNA nucleotides 1928 to 2314, followed by a poly A tail, permitting replication and packaging in the presence of helper virus such that said infectious Sindbis DI alphavirus is capable upon infection of a host cell of expressing said protein coding sequence.

* * * * *